(12) United States Patent
Zhai et al.

(10) Patent No.: US 7,214,804 B2
(45) Date of Patent: May 8, 2007

(54) HETEROCYCLIC COMPOUNDS USEFUL AS GROWTH HORMONE SECRETAGOGUES

(75) Inventors: Weixu Zhai, Middletown, CT (US);
Samuel Gerritz, Guilford, CT (US);
Charles John Andres, Jr., Wethersfield, CT (US); Joseph A. Tino, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 75 days.

(21) Appl. No.: 11/033,649

(22) Filed: Jan. 12, 2005

(65) Prior Publication Data
US 2005/0154043 A1 Jul. 14, 2005

Related U.S. Application Data

(60) Provisional application No. 60/536,128, filed on Jan. 13, 2004.

(51) Int. Cl.
*C07D 207/06* (2006.01)
*A61K 31/40* (2006.01)

(52) U.S. Cl. ..................... 548/568; 514/428
(58) Field of Classification Search ............ 548/568; 514/428
See application file for complete search history.

(56) References Cited

U.S. PATENT DOCUMENTS 5,622,973 A 4/1997 Morriello et al.

FOREIGN PATENT DOCUMENTS

| EP | 1 002 802 | 5/2000 |
|----|-----------|--------|
| WO | WO 00/54729 | 9/2000 |

OTHER PUBLICATIONS

Ankersen, M. et al., "Growth hormone secretagogues: recent advances and applications", Drug Discovery Today, vol. 4, No. 11, pp. 497-506 (1999).
Svensson, J., "Growth hormone secretagogues", Expert Opinion on Therapeutic Patents, vol. 10, No. 7, pp. 1071-1080 (2000).
Database CA 'Online! Chemical Abstracts Service, Columbus, Ohio, US, Kiyooka, Syunichi et al: "Synthesis of optically active beta-hydroxy acids having no substituent at alpha-position by aldol reaction" XP002336877 retrieved from STN Database accession No. 1985:5414126 RN 98352-25-1 abstract & Kochi Daigaku Rigakubu Kiyo, Kagaku, 6, 9-14 Coden: KDRKDD; ISSN: 0389-0279, 1985.

*Primary Examiner*—Kamal A. Saeed
*Assistant Examiner*—Michael P. Barker
(74) *Attorney, Agent, or Firm*—Sammy G. Duncan, Jr.

(57) ABSTRACT

The present invention relates to novel heterocyclic compounds, according to Formula I, that stimulate endogenous production and/or release of growth hormone, wherein $R_1$, $R_2$, $R_3$, $R_4$ and X are defined herein. Further, the present invention relates to methods for using such compounds and to pharmaceutical compositions containing such compounds

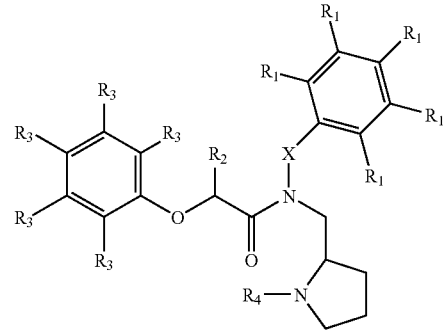

Formula I

5 Claims, No Drawings

HETEROCYCLIC COMPOUNDS USEFUL AS GROWTH HORMONE SECRETAGOGUES

RELATED APPLICATIONS

This application claims priority benefit under Title 35 § 119(e) of U.S. provisional Application No. 60/536,128, filed Jan. 13, 2004, the contents of which are herein incorporated by reference.

BACKGROUND OF THE INVENTION

Growth hormone is important not only for linear body growth, but is also important for the maintenance of body composition, metabolism and heart function in adult life. In fact, treatment with growth hormone is employed in both adults and children suffering from growth hormone deficiency. Treatment with growth hormone has been shown to reduce body fat, increase fat-free mass, increase muscle strength, improve bone mass and well-being. These beneficial effects associated with growth hormone treatment suggest that growth hormone treatment may further be useful for the treatment of osteoporosis, frailty in the elderly, complicated fracture, cardiomyopathy, obesity and some nitrogen-wasting conditions resulting from, for example, AIDS, chronic dialysis, catabolic disease and glucocorticoid treatment. Johan Svensson, *Exp. Opin. Ther. Patents*, 2000 10(7) 1071–1080; Ankersen et al., *DDT*, 1999, 4(11) 497–506. Moreover, growth hormone therapy is also been explored with a view towards reversing changes associated with aging.

Current methods for administering growth hormone are invasive in that synthetic growth hormone must be administered by daily injection. Therefore, if an orally administered secretagogue could be introduced that is safe, efficacious, well tolerated, it would provide an attractive treatment alternative to current growth hormone treatment.

Growth hormone secretagogues are synthetically produced peptides and non-peptides that stimulate the endogenous production and/or release of growth hormone by acting on one or more specific receptors at both pituitary and hypothalamic levels. Accordingly, orally active growth hormone secretagogues could offer attractive alternatives to traditional growth hormone therapy, thus providing a more convenient means to treat a wider array of diseases or disorders associated with growth hormone levels in patient circulation.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I

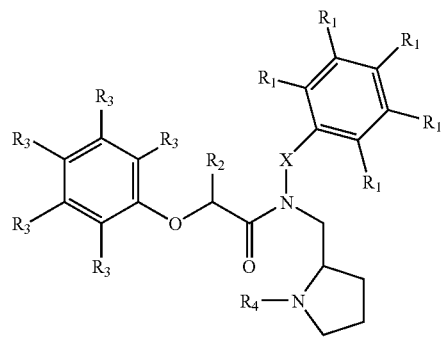

Formula I including all prodrugs, pharmaceutically acceptable salts and stereoisomers, $R_1$, $R_2$, $R_3$, $R_4$ and X are described herein:

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

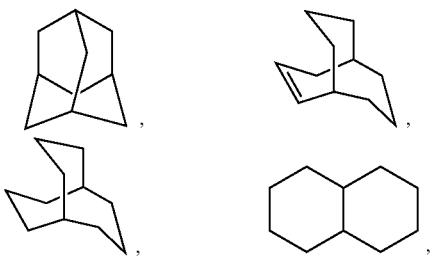

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, alkenyl, alyalkynyl, oxyperfluoroalkyl (e.g. —$OCF_3$), oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl, The term "carbo" as used herein as part of another group refers to a carbonyl (C=O) group serving as a linker between two groups such as, for example, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl and thiocycloalkyl.

The term "perfluoro" as used herein as part of another group refers to a group wherein more than one hyrdogen atom attached to one or more carbon atoms in the group has been replaced with a fluorine atom such as, for example, perfluoroalkyl (e.g. —$CF_3$), perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfo" as used herein as part of another group refers to an —SO$_2$— group such as, for example, sulfalkyl, sulfoalkenyl, sulfoalkynyl, sulfoaryl, sulfocycloalkyl, sulfoheterocyclyl and sulfoheteroaryl.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch. 5, pgs 113–191 (Harwood Academic Publishers, 1991).

Said references are incorporated herein by reference.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

General Synthetic Schemes

The compounds of the present invention may be prepared according to the following general synthetic reaction schemes as well as relevant published literature procedures that may be used by one skilled in the art. Exemplary reagents, procedures and conditions for these reactions appear hereinafter and in the working examples. Starting materials are commercially available or can be readily prepared by one of ordinary skill in the art using known methods. Unless otherwise specified the various substituents of the compounds are defined in the same manner as the formula I.

High Speed Analoging (HSA) may be employed in the preparation of compounds, for example, where the intermediates possess an amine position or activated aromatic position, such as the halogenated Q1 and Q2.

Scheme I

As illustrated in Scheme 1, compounds of Formula I may be prepared through the attachment of prolinol to a solid support of formula II via a carbamate linkage to produce solid-supported compound of formula III. Solid supports of formula II are available commercially or may be prepared from solid supports equipped with the Wang linker by treatment with p-nitrophenylchloroformate and a mild base in an inert solvent. Oxidation of the free hydroxyl group of compound of formula III using methods known in the literature provides solid-supported compound of formula IV, which upon treatment with amine of formula V and a mild reducing agent such as sodium triacetoxyborohydride in a polar solvent such as dimethylformamide provides solid-supported compound of formula VI. Solid-supported compound of formula VIII may be prepared by treatment of compound of formula VI with an acid chloride of formula VII in the presence of a tertiary amine base and an inert solvent such as dichloromethane. Treatment of solid-supported compound of formula VIII with a strong acid such as trifluoroacetic acid provides compound of formula I.

SCHEME 1

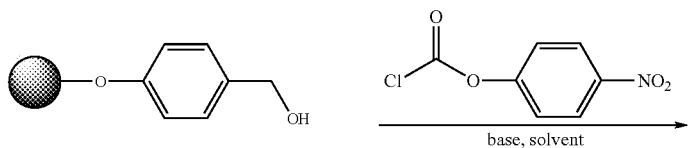

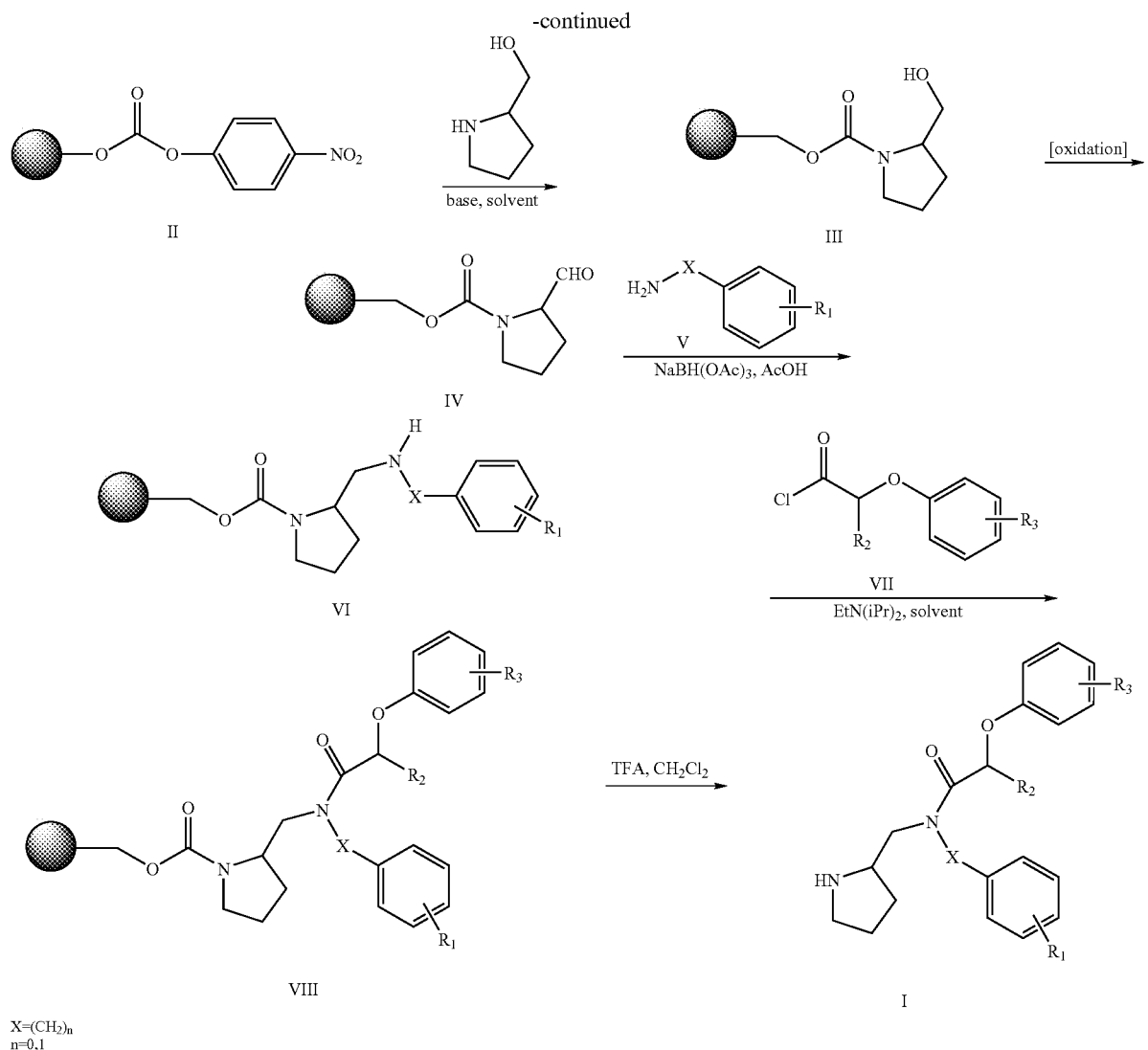

Scheme II

As illustrated in Scheme II, compounds of Formula I may be prepared through the attachment of prolinol to the solid support via a Michael reaction with REM resin (commercially available) to produce solid-supported compound of formula IX. Oxidation of the free hydroxyl group of compound of formula IX using methods known in the literature provides the solid-supported compound of formula X, which upon treatment with amine of formula V and a mild reducing agent such as sodium triacetoxyborohydride provides solid-supported compound of formula XI. Solid-supported compound of formula XII may be prepared by treatment of compound of formula XI with an acid chloride of formula VII in the presence of a tertiary amine base and an inert solvent such as dichloromethane. Treatment of solid-supported compound of formula XII with an alkylating agent such as methyl iodide provides solid-supported compounds of formula XIII. Treatment of solid-supported compound of formula XIII with a mild base such as triethylamine provides compound of formula I.

SCHEME II

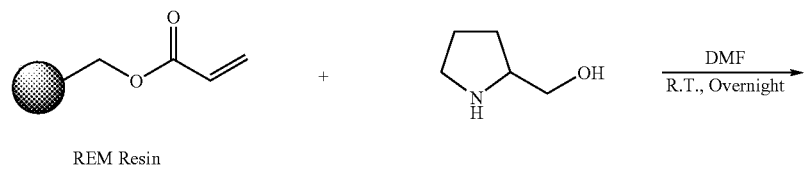

REM Resin

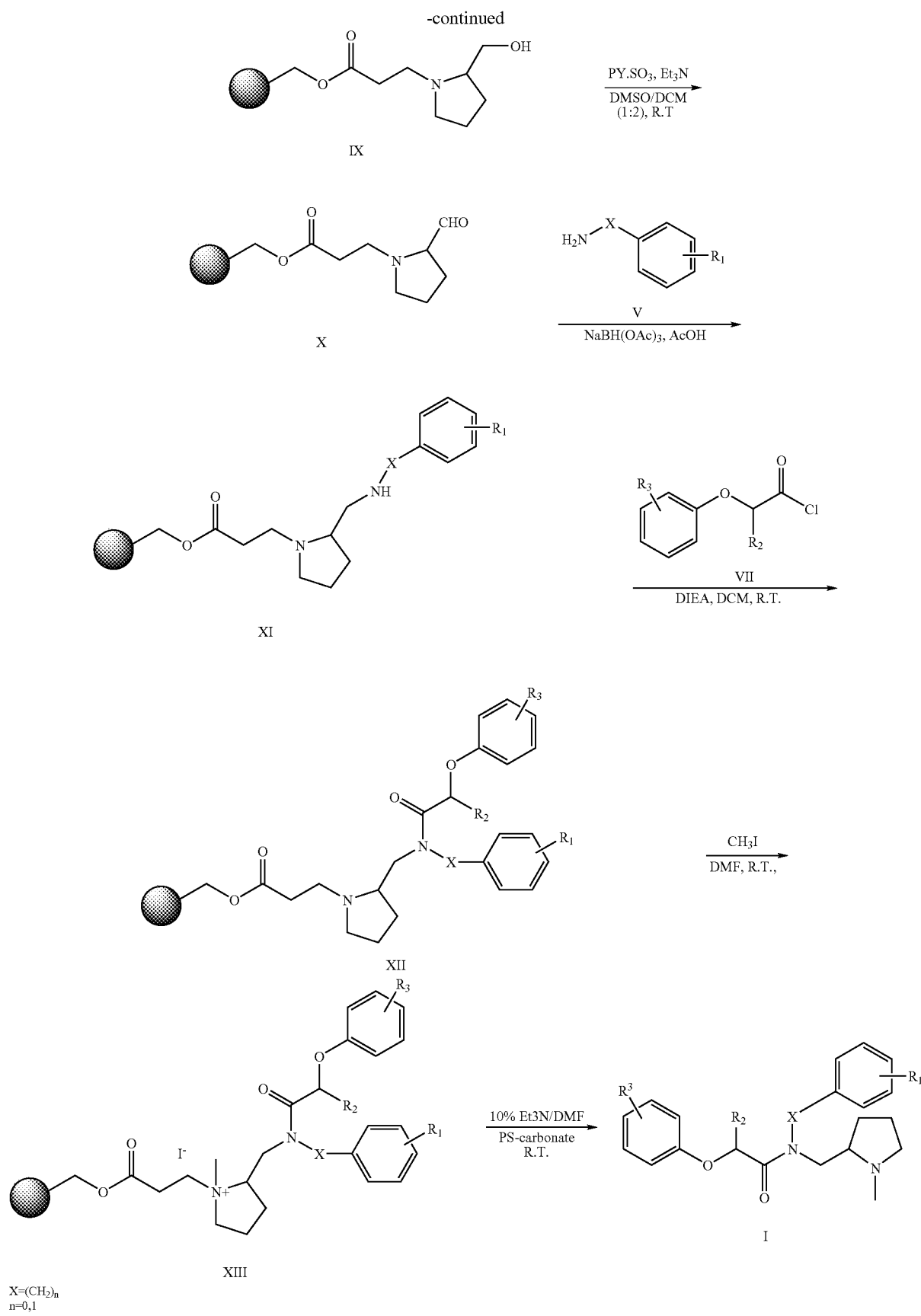

Utilities and Combinations

Utilities

The growth hormone releasing compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed compounds of Formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of Formula I of the invention is in combination with parathyroid hormone or bisphosphonates, such as MK-217 (alendronate), in the treatment of osteoporosis.

A still further use of the disclosed compounds of Formula I is in combination with estrogen, testosterone, a selective estrogen receptor modulator, such as tamoxifen or raloxifene, or a selective androgen receptor modulator, such as disclosed in Edwards, J. P. et al., *Bio. Med. Chem. Let.*, 9, 1003–1008 (1999) and Hamann, L. G. et al., *J. Med. Chem.*, 42, 210–212 (1999), for the treatment of aspects of Metabolic Syndrome, maintenance of muscle strength and function in elderly humans, reversal or prevention of fraility in elderly humans, stimulation and increase in muscle mass and muscle strength, attenuation of protein catabolic response after a major operation or trauma; reducing cachexia and protein loss due to chronic illness such as cancer or AIDS; improvement in muscle mobility, and maintenance of skin thickness.

A further use of the compounds of this invention is in combination with progestin receptor agonists ("PRA").

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself.

To those skilled in the art, it is well known that the current and potential uses of growth hormone are varied and multitudinous. Thus, compounds of Formula I can be administered for purposes stimulating release of endogenous growth hormone and would thus have similar effects or uses as growth hormone itself. Compounds of Formula I are useful for stimulation of growth hormone release (e.g., in the elderly); maintenance of muscle strength and function (e.g., in the elderly); reversal or prevention of fraility or age-related functional decline ("ARFD") in the elderly; prevention of catabolic side effects of glucocorticoids; prevention and treatment of osteoporosis; treatment of chronic fatigue syndrome ("CFS"); treatment of acute fatigue syndrome and muscle loss following election surgery; stimulation of the immune system, including improvement of immune response to vaccination; acceleration of wound healing; accelerating bone fracture repair (such as accelerating the recovery of hip fracture patients); accelerating healing of complicated fractures, e.g. disctraction osteogenesis; acceleration of tooth repair or growth; maintenance of sensory function (e.g., hearing, sight, olefaction and taste); treatment of wasting secondary to fractures; treatment of growth retardation; treatment of growth retardation resulting from renal failure or insufficiency; treatment of cardiomyopathy; treatment of wasting in connection with chronic liver disease; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of wasting in connection with chronic obstructive pulmonary disease ("COPD"); treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of growth retardation associated with the Prader-Willi syndrome and Turner's syndrome; increasing the growth rate of a patient having partial growth hormone insensitive syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients; treatment of osteochondrodysplasias; treatment of Noonan's syndrome; treatment of schizophrenia; treatment of depression; improvement of cognitive function (e.g., treatment of dementia; treatment of Alzheimer's disease; treatment of delayed wound healing and psychosocial deprivation; treatment of catabolism in connection with pulmonary dysfunction and ventilator dependency; treatment of cardiac dysfunction (e.g. associated with valvular disease, myocarial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD, etc.); reducing cachexia and protein loss due to chronic illness such as cancer or AIDS; treatment of hyperinsulinemia including nesidioblastosis; adjuvant treatment for ovulation induction; stimulation of thymic development and prevention of the age-related decline of thymic function; treatment of immunosuppressed patients; treatment of sarcopenia; treatment of wasting in connection with AIDS; treatment of wasting in connection with multiple sclerosis or other neurodegenerative disorders; improvement in muscle strength, mobility, maintenance of skin thickness; hair/nail growth; treatment of metabolic homeostasis and renal homeostasis (e.g., in the frail elderly); stimulation of osteoblasts, bone remodelling and cartilage growth; regulation of food intake;

stimulation of the immune system in companion animals and treatment of disorders of aging in companion animals; promoting growth in livestock; stimulation of wool growth in sheep; increasing milk production in livestock; treatment of insulin resistance including NIDDM, in mammals (e.g. humans); treatment of insulin resistance in the heart; improvement of sleep quality and correction of the relative hyposomatotropism of senescence due to high increase in REM sleep and a decrease in REM latency; treatment of hypothermia; treatment of frailty such as that associated with aging; treatment of congestive heart failure; treatment of hip fractures; treatment of immune deficiency in individuals with a depressed T4/T8 cell ratio; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in elderly); enhancing the activity of protein kinase B (PKB); improvement of the overall pulmonary function; treatment of sleep disorders; and the treatment of the catabolic state of prolonged critical illness. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

Combinations

The compounds of the present invention may be employed alone or in combination with each other and/or other growth hormone secretagogues or other suitable therapeutic agents useful in the treatment of the aforementioned disorders including: anti-diabetic agents; anti-osteoporosous agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroespheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519,079 filed Mar. 6, 2000, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin lovastatin, atorvastatin, simvastatin, NK-104 (a.k.a. itavastatin, or nisvastatin or nisbastatin) and ZD-4522

(a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitiors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Compounds of the present invention may further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B 12, folate, C, D and E), minerals (e.g., selenium, magnesium, zinc, chromium, calcium and potassium), carnitine, lipoic acid, creatine, and coenzyme Q-10.

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

EXAMPLES

The following Examples represent preferred embodiments of the invention. All temperatures are in ° C. unless indicated otherwise.

Example 1

2-(3-Chlorophenoxy-N-(2-Chlorobenzyl)-N—(R-)-pyrrolidin-2-ylmethyl-propionamide

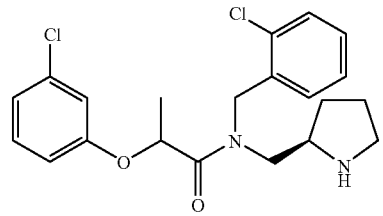

1A: 4-nitrophenylcarbonate Wang Resin

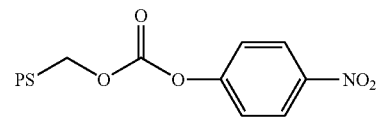

To a suspension of 50 g of Wang resin (1.3 mMol/g, 65.0 mmol, 1.0 eq.) in 800 ml of anhydrous dichloromethane (DCM) was added 39.3 g of 4-nitrophenyl chloroformate (195.0 mmol, 3.0 eq.), and 29.0 ml of N-methylmorpholine (NMM, 260 mmol, 4.0 eq.) at room temperature. The resulting mixture was shaken at room temperature overnight. Filtered and washed with DCM (4×500 ml), ether (2×500 ml), dried under house vacuum overnight to afford 74.5 g of 4-nitrophenylcarbonate Wang resin.

1B

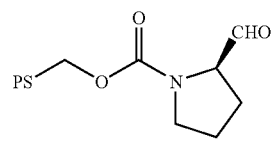

16.2 g of the 4-nitrophenylcarbonate Wang resin prepared as above was filled into 462 Microkans (from IRORI company, ~35 mg resin/Microkan, 21.06 mmol, 1.0 eq.). The Microkans were placed in a 2000 ml flask, to which 1000 ml of anhydrous DCM was added, followed by addition of 10.63 g of 2-(R)-(−)-pyrrolidinemethanol(105.1 mmol, 5.0 eq.), and 14.7 ml of triethylamine(105.1 mmol, 5.0 eq.) at room temperature. The reaction flask was shaken at room temperature for 18 hrs. The resin was washed with DCM (3×400 ml) and methanol(3×400 ml), then dried under house vacuum overnight. Separately, to a solution of sulfur trioxide-pyridine complex (33.45 g, 210 mmol, 10.0 eq.) in 900 ml of 2/1 DCM/dimethyl sulfoxide(DMSO) was added 58.5 ml of triethylamine (420 mmol, 20.0 eq.) at room temperature. The resulting mixture was stirred at room temperature for 30 min., then the Microkans were added and the reaction vessel was shaken for 3 hrs. The resin was washed with DCM (2×1000 ml), DMF(3×1000 ml), THF (2×1000 ml), DCM (2×1000 ml), then dried under house vacuum overnight.

1C

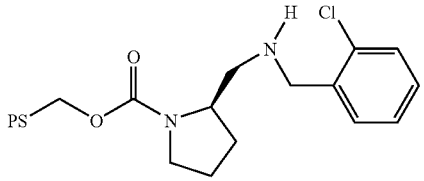

To a reaction vessel with the above Microkans was added 2.5 ml per Microkan of 7/3 DMF/trimethyl orthoformate (TMOF), 2-chlorobenzylamine (15.0 eq.), acetic acid (50 μl per Microkan), and NaBH(OAc)$_3$ (15.0 eq.). The reaction vessel was shaken at room temperature for 2 days. The resin was washed with DMF (4×3 ml/Microkan), 2/1 DMF/MeOH(3×3 ml/Microkan), THF(2×3 ml/microkan), DCM (2×3 ml/Microkan), then dried under house vacuum overnight.

1D: 2-(3-Chlorophenoxy-N-(2-Chlorobenzyl)-N—(R-)-pyrrolidin-2-ylmethyl-propionamide:

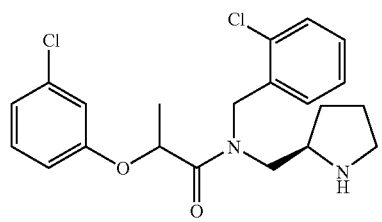

To a solution of (3-chlorophenoxy)propionic acid (5.0 eq.) in anhydrous DCM was added oxalyl chloride (4.5 eq., 2M solution in DCM), and a few drops of DMF. The resulting mixture was stirred at room temperature for 1 hr, then transferred to a reaction vessel containing the dried Microkan, DCM (2 ml per Microkan) and triethylamine (25.0 eq.). The reaction vessel was shaken for 2 days. Washed with DCM (3×3 ml/Microkan), DMF(3×3 ml/Microkan), THF(3×3 ml/Microkan), DCM (2×3 ml/Microkan).

After the Microkan was dried under house vacuum overnight, the resin was treated with 50% trifluoroacetic acid (TFA) in DCM at room temperature for 1 hr. The resin was filtered and the filtrate was concentrated to provide the crude product, which was purified by preparative HPLC affording 7.35 mg of oil as the desired product, yield: 43.3% based on the theoretical loading of the Wang resin. $^1$H-NMR(CD$_3$OD, 500 MHz): δ7.47–6.62(m, 8H), 5.26(q, 1H, J=6), 4.92(s, 2H), 3.81–3.65(m, 1H), 3.2–3.5(m, 4H), 2.11–2.09(m, 2H), 1.95–1.90(m, 1H), 1.71–1.68(m, 1H), 1.59(d, 3H, J=6.5); MS(ESP+)m/e: 407(MH$^+$); Tr=1.53 min.

Example 2

N-(4-Acetylamino-phenyl)-2-(3-chlorophenoxy)-N—(R)-pyrrolidin-2-ylmethyl-propionamide

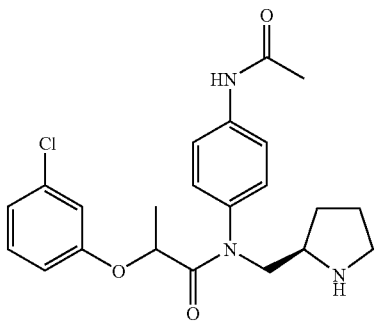

The title compound was prepared according to the procedures of Example 1 to give 11 mg of oil as the product (53% yield based on the theoretical loading of the Wang resin. $^1$H NMR(CD$_3$OD, 500 MHz) δ 7.69(d, 2H, J=14), 7.32(d, 2H, J=11), 7.20(t, 1H, J=13.5), 6.94–6.62(m, 3H), 4.78(q, 1H, J=11), 3.84–3.3.70(m, 2H), 3.36–3.3.28(m, 3H), 2.13(s, 3H), 2.08–2.0(m, 3H), 1.81–1.62(m, 1H), 1.44(d, 3H, J=6); MS(ESP+)m/e: 416(MH$^+$); Tr=1.29 min.

Example 3

N-Benzyl-2-phenoxy-N—(R)-pyrrolidin-2-ylmethyl-butyramide

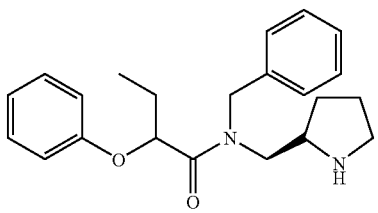

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=0.82 min.; MS(ESP+) m/e 353(MH$^+$).

Example 4

2-Phenoxy-N-pyrrolidin-2-ylmethyl-N-(4-trifluoromethoxybenzyl)propionamide

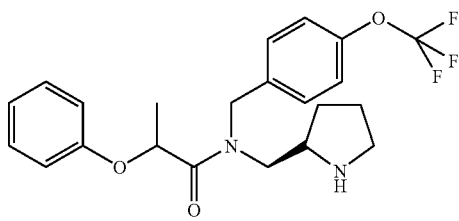

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=0.98 min.; MS(ESP+) m/e 423(MH$^+$).

Example 5

2-Phenoxy-N-pyrrolidin-2-ylmethyl-N-(4-trifluoromethoxybenzyl)butyramide

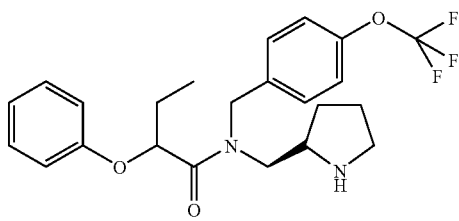

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=0.98 min.; MS(ESP+) m/e 437(MH$^+$).

Example 6

N-(2-methylbenzyl)-2-phenoxy-N-pyrrolidin-2-ylmethyl-butyramide

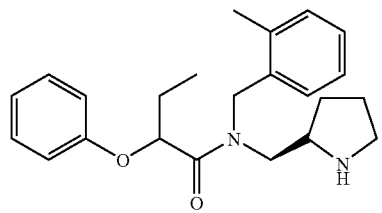

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=1.52 min.; MS(ESP+) m/e 367(MH$^+$).

Example 7

N-(3-fluorobenzyl)-2-phenoxy-N-pyrrolidin-2-ylmethyl-butyramide

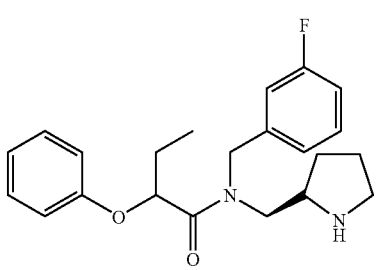

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=min.; MS(ESP+) m/e 371(MH$^+$).

Example 8

N-(3-chlorobenzyl)-2-phenoxy-N-pyrrolidin-2-ylmethyl-propionamide

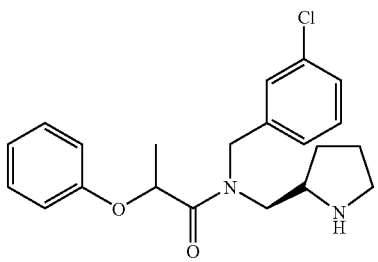

The title compound was prepared according the method of Example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=1.45 min.; MS(ESP+) m/e 373(MH$^+$).

Example 9

N-(2-methylbenzyl)-2-phenoxy-N—(R)-pyrrolidin-2-ylmethyl-propionamide

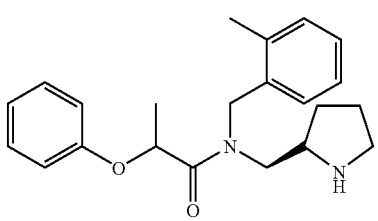

The title compound was prepared according the method of Example 1. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.42 min.; MS(ESP+) m/e 353(MH⁺).

Example 10

N-(2-methylbenzyl)-2-phenoxy-N—(S)-pyrrolidin-2-ylmethyl-propionamide

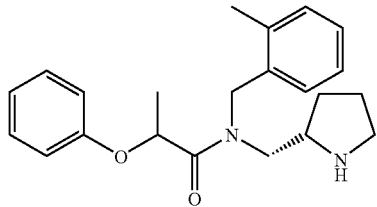

The title compound was prepared according the method of specific example 1. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.43 min.; MS(ESP+) m/e 353(MH⁺).

Example 11

N-(3-fluorobenzyl)-2-phenoxy-N—(R)-pyrrolidin-2-ylmethyl-propionamide

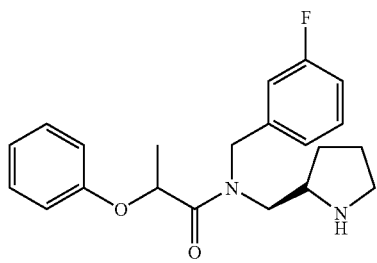

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=0.98 min.; MS(ESP+) m/e 357(MH⁺).

Example 12

N-(3-methoxybenzyl)-2-phenoxy-N—(R)-pyrrolidin-2-ylmethyl-propionamide

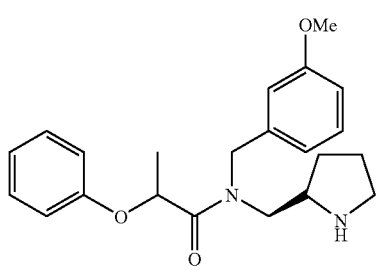

The title compound was prepared according the method of specific example 1. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.35 min.; MS(ESP+) m/e 369(MH⁺).

Example 13

N-(3-methylbenzyl)-2-phenoxy-N—(R)-pyrrolidin-2-ylmethyl-propionamide

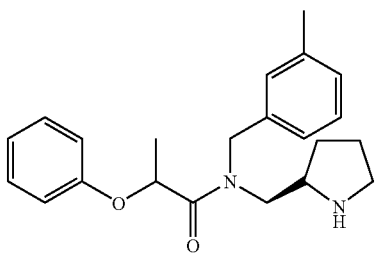

The title compound was prepared according the method of specific example 1. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.43 min.; MS(ESP+) m/e 353(MH⁺).

Example 14

N-(3-methylbenzyl)-2-phenoxy-N—(R)-pyrrolidin-2-ylmethyl-butyramide

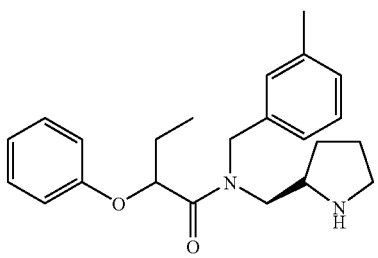

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.06 min.; MS(ESP+) m/e 367(MH⁺).

Example 15

N-(4-fluorobenzyl)-2-phenoxy-N—(R)-pyrrolidin-2-ylmethyl-propionamide

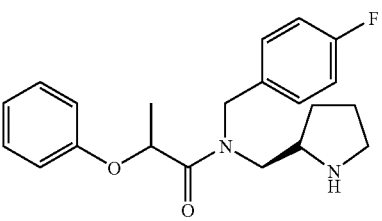

The title compound was prepared according the method of specific example 1. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.43 min.; MS(ESP+) m/e 357(MH+).

Example 16

N-(4-chlorobenzyl)-2-(3-chlorophenoxy-N—(R)-pyrrolidin-2-ylmethyl-propionamide

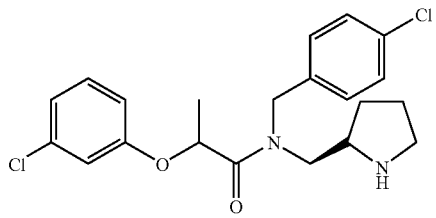

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.02 min.; MS(ESP+) m/e 407(MH+).

Example 17

N-(2-methylbenzyl)-2-(3-methylphenoxy-N—(R)-pyrrolidin-2-ylmethyl-propionamide

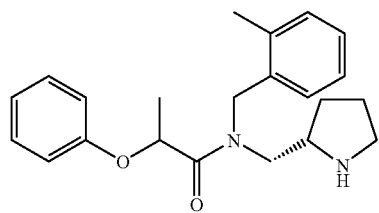

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.), Tr=0.78 min.; MS(ESP+) m/e 353(MH+).

Example 18

N-(2-chlorobenzyl)-2-(3-chlorophenoxy-N—(R)-pyrrolidin-2-ylmethyl-propionamide

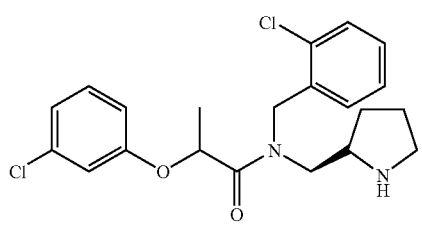

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.08 min.; MS(ESP+) m/e 407(MH+).

Example 19

N-(2-methylbenzyl)-2-(3-chlorophenoxy-N—(R)-pyrrolidin-2-ylmethyl-propionamide

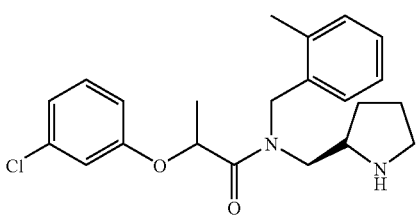

The title compound was prepared according the method of specific example 1. HPLC(XTERRA 2.1×50 mm, 100% H₂O with 0.1% TFA to 100% CH₃CN with 0.1% TFA, gradient 2 min., flow rate=4 ml/min.) Tr=1.07 min.; MS(ESP+) m/e 387(MH+).

Example 20

N-(3-methylbenzyl)-2-(2-chlorophenoxy-N—(R)-pyrrolidin-2-ylmethyl-propionamide

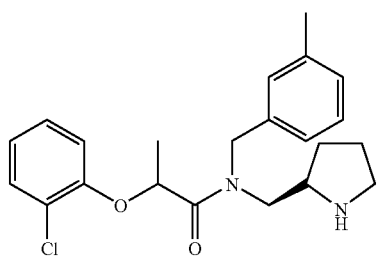

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.07 min.; MS(ESP+) m/e 387(MH+).

Example 21

2-(3-Chlorophenoxy)-N-(3-methylbenzyl)-N—(R)-pyrrolidin-2-ylmethyl-propionamide

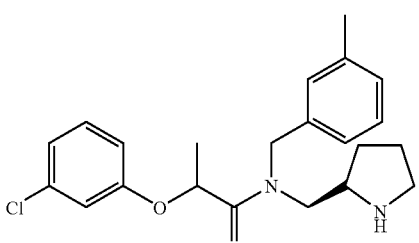

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.04 min.; MS(ESP+) m/e 387(MH⁺).

Example 22

2-(3-Chlorophenoxy)-N-(4-methoxylbenzyl)-N—(R)-pyrrolidin-2-ylmethyl-propionamide

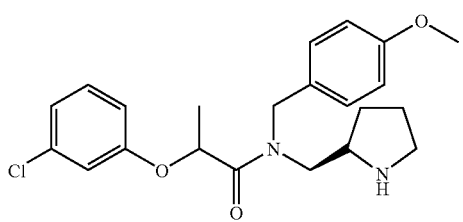

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=0.99 min.; MS(ESP+) m/e 403(MH⁺).

Example 23

N-(3-chlorobenzyl)-2-(2-Chlorophenoxy)-N—(R)-pyrrolidin-2-ylmethyl-propionamide

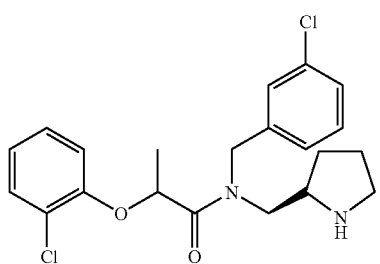

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.08 min.; MS(ESP+) m/e 407(MH⁺).

Example 24

N-(3-chlorobenzyl)-2-(3-Chlorophenoxy)-N—(R)-pyrrolidin-2-ylmethyl-propionamide

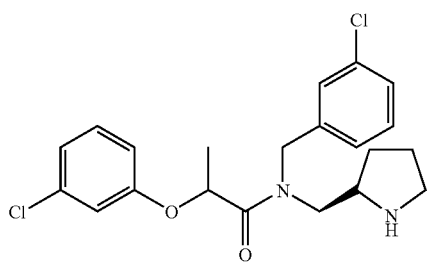

The title compound was prepared according the method of specific example 1. HPLC(XTERRA 2.1×50 mm, 100% H₂O with 0.1% TFA to 100% CH₃CN with 0.1% TFA, gradient 2 min., flow rate=4 ml/min.) Tr=1.02 min.; MS(ESP+) m/e 407(MH⁺).

Example 25

N-(4-acetylaminophenyl)-2-phenoxy-N—(R)-pyrrolidin-2-ylmethyl-propionamide

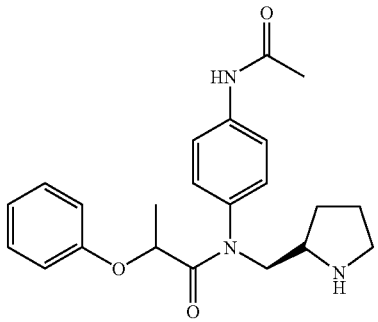

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.), Tr=1.15 min.; MS(ESP+) m/e 382(MH⁺).

Example 26

N-(2,4-dimethoxyphenyl)-2-phenoxy-N—(R)-pyrrolidin-2-ylmethyl-propionamide

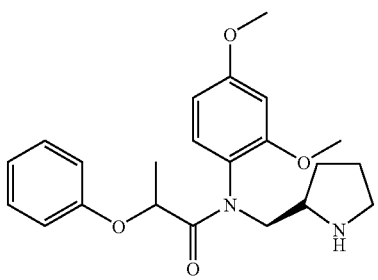

The title compound was prepared according the method of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.12 min.; MS(ESP+) m/e 385(MH⁺).

Example 27

N-Biphen-3-yl-2-phenoxy-N—(R)-pyrrolidin-2-ylmethyl-propionamide

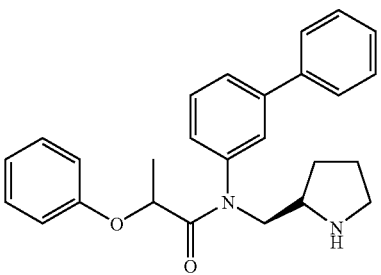

The title compound was prepared according the method of specific example 1. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=1.29 min.; MS(ESP+) m/e 401(MH$^+$).

Example 28

(2-Chlorophenoxy)-N-(2-chlorophenyl)-N—(R)-pyrrolidin-2-ylmethyl-acetamide

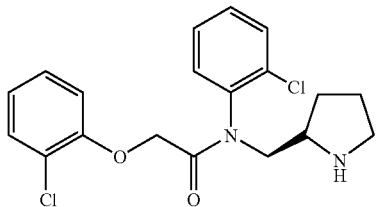

The title compound was prepared according the method of specific example 1. HPLC (XTERRA 2.1×50 mm, 100% H$_2$O with 0.1% TFA to 100% CH$_3$CN with 0.1% TFA, gradient 2 min., flow rate=4 ml/min.), Tr=0.92 min.; MS(ESP+) m/e 379(MH$^+$).

Example 29

N-(4-Acetylaminophenyl)-2-(3-chlorophenoxy)-N—(R)-pyrrolidin-2-ylmethyl-acetamide

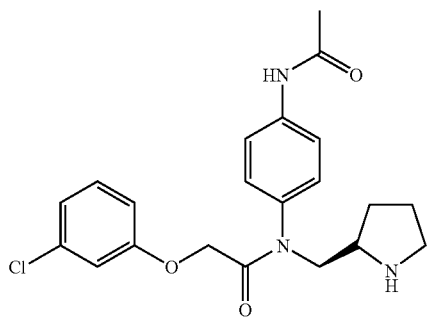

The title compound was prepared according the method of specific example 1. HPLC (XTERRA 2.1×50 mm, 100% H$_2$O with 0.1% TFA to 100% CH$_3$CN with 0.1% TFA, gradient 2 min., flow rate=4 ml/min.) Tr=0.90 min.; MS(ESP+) m/e 402(MH$^+$).

Example 30

N-(4-Acetylaminophenyl)-N-[1-methyl-(R)-pyrrolidin-2-ylmethyl]-2-phenoxypropionamide

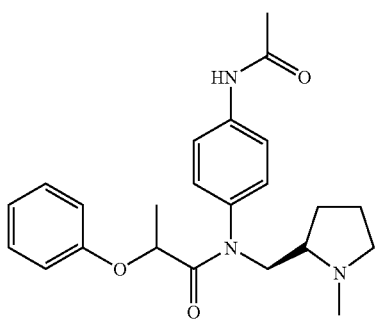

The title compound was prepared according the protocols shown in Scheme 2. To a suspension of 2 g of REM resin (1.0 mmol/g, 1.0 eq.) in 15 ml of DMF was added (R)-(−)-pyrrolidinemethanol(1.01 g, 5.0 eq.). The reaction vessel was shaken at room temperature overnight. Filtered and washed with DMF(20 ml×3), THF(20 ml×3), MeOH(20 ml×3), dried in vacuo overnight.

Separately, to a solution of sulfur trioxide-pyridine complex(3.31 g, 10.0 eq.) in 2/1 DCM/DMSO (30 ml) was added triethylamine (5.8 ml, 20.0 eq.). The resulting mixture was stirred at room temperature for 30 min. Transferred this solution to a reaction vessel which was containing the resin as above. The resulting suspension was shaken at room temperature for 3 hrs. Filtered and washed with DCM(20 ml×3), MeOH (20 ml×3), dried in vacuo overnight.

To a suspension of 600 mg of the above resin in 7/3 DMF/TMOF (10 ml) was added 4'-aminoacetoanilide (15.0 eq., 1.35 g), 200 μl of acetic acid, followed by the addition of NaBH(OAc)$_3$ (1.91 g, 15.0 eq.). The resulting mixture was shaken at room temperature for two days. Filtered and washed with DMF(10 ml×4), MeOH(10 ml×4), THF(10 ml×2), MeOH(10 ml×2), dried in vacuo overnight.

The above resin was filled into Microkans (35 mg/kan). To a reaction vessel containing the Microkans was added anhydrous DCM (3 ml per Microkan), 2-phenoxyacetyl chloride (5.0 eq.), and DIEA (10.0 eq.). The reaction vessel was shaken at room temperature for 2 day, then washed with DCM(3 ml/kan×3), DMF(3 ml/kan×3), 1/1 DMF/MeOH(3 ml/kan×3), THF(3 ml/kan×2), DCM(3 ml/kan×2), and dried in vacuo overnight.

To a reaction vessel containing the above microkans was added DMF(3 ml/kan), and iodomethane(10.0 eq.). The reaction vessel was shaken at room temperature for 24 hrs. Washed with DMF(3 ml/kan×3), THF(3 ml/kan×3), DCM(3 ml/kan×3), dried in vacuo overnight. Each Microkan, after being dried in vacuo overnight, was treated with 10% triethylamine in DMF and 100 mg (2.5 mMol/g) of polystyrene-supported carbonate and shaken vigorously for 24 hrs. The resin was filtered and washed with 2 ml of MeOH. The combined filtrates were concentrated in vacuo to afford the crude product as an oil, which was purified by preparative HPLC to afford the desired product. HPLC (XTERRA 3.0×50 mm, 10% MeOH/90% H$_2$O/0.1% TFA to 90% MeOH/10% H$_2$O/0.1% TFA, gradient 2 min., flow rate=5 ml/min.), Tr=1.093 min.; MS(ESP+) m/e 396(MH$^+$).

Example 31

N-(4-Acetylaminophenyl)-N-[1-methyl-(R)-pyrrolidin-2-ylmethyl]-2-phenoxybutyramide

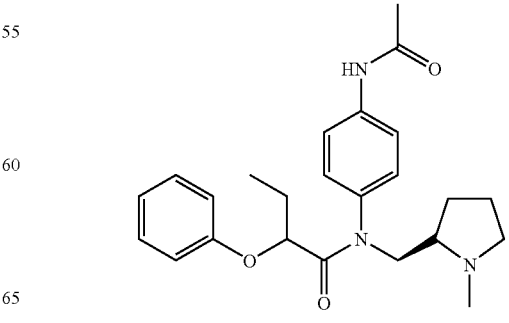

The title compound was prepared according the method of specific example 30. HPLC (XTERRA 3.0×50 mm, 10% MeOH/90% H₂O/0.1% TFA to 90% MeOH/10% H₂O/0.1% TFA, gradient 2 min., flow rate=5 ml/min.), Tr=1.207 min.; MS(ESP+) m/e 410(MH⁺).

Example 32

N-(4-acetoaminophenyl)-2-(3-chlorophenoxy)-N—(R)-pyrrolidin-2-ylmethyl-propionamide

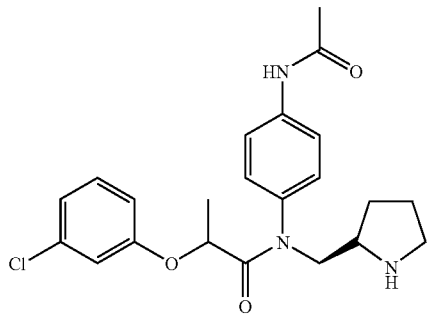

The title compound was prepared according the methods of specific example 1. HPLC (XTERRA 2.1×50 mm, 100% H₂O with 0.1% TFA to 100% CH₃CN with 0.1% TFA, gradient 2 min., flow rate=4 ml/min.) Tr=0.98 min.; MS(ESP+) m/e 416(MH⁺).

Example 33

2-(3-chlorpheoxy)-N-(3-chlorophenyl)-N—(R)-pyrrolidin-2-ylmethyl-propionamide

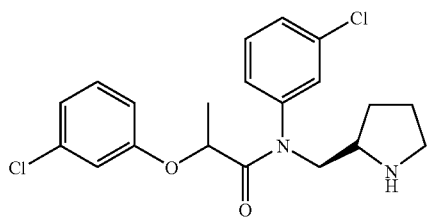

The title compound was prepared according the methods of specific example 1. HPLC (XTERRA 2.1×50 mm, 100% H₂O with 0.1% TFA to 100% CH₃CN with 0.1% TFA, gradient 2 min., flow rate=4 ml/min.) Tr=1.06 min.; MS(ESP+) m/e 393(MH⁺).

Example 34

N-(4-acetoaminophenyl)-N—(R)-pyrrolidin-2-ylmethyl-2-m-tolyloxyacetoamide

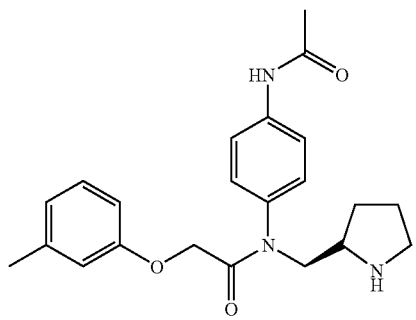

The title compound was prepared according the methods of specific example 1. HPLC (XTERRA 2.1×50 mm, 100% H₂O with 0.1% TFA to 100% CH₃CN with 0.1% TFA, gradient 2 min., flow rate=4 ml/min.) Tr=0.93 min.; MS(ESP+) m/e 382(MH⁺).

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to Formula I:

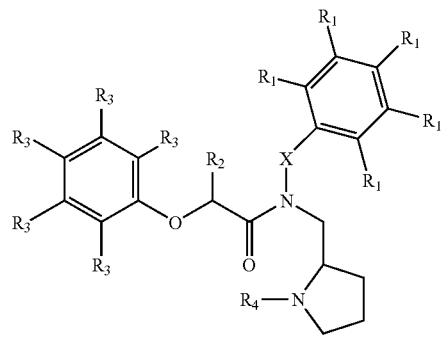

Formula I wherein, $R_1$ at each occurrence is independently selected from the group consisting of hydrogen, alkyl, aryl, hydroxy, oxyalkyl, oxyperfluoroalkyl halo, amino, carboaminoalkyl, aminocarboalkyl and carboaminocarboalkyl, wherein each alkyl, aryl, oxyalkyl, amino, carboaminoalkyl, aminocarboalkyl and carboaminocarboalkyl, may optionally be substituted with one or more alkyl, aryl, hydroxy, oxyalkyl, oxyperfluroalkyl, halo, amino, carboaminoalkyl, aminoarboalkyl or carboaminocarboalkyl;

$R_2$ is selected from the group consisting of H and alkyl;

$R_3$ at each occurrence is independently selected from the group consisting of hydrogen, alkyl and halo;

$R_4$ is selected from the group consisting of H and alkyl;

X is $(CH_2)_n$; and n is 0 or 1, wherein Formula I is inclusive of all prodrugs, prodrug esters, stereoisomers and pharmaceutically acceptable salts of Formula I.

2. The compound according to claim 1, wherein:
$R_1$ at each occurrence is independently selected from the group consisting of hydrogen, alkyl, aryl, oxyalkyl, oxyperfluoroalkyl and aminocarboalkyl.

3. A pharmaceutical composition, comprising
at least one compound according to claim 1; and
at least one pharmaceutically acceptable adjuvant or carrier.

4. The pharmaceutical composition according to claim 3, further comprising: at least one additional therapeutic agent selected from the group consisting of other compounds of formula I, parathyroid hormone, bisphosphonates, estrogen, testosterone, selective estrogen receptor modulators, selective androgen receptor modulators, progestin receptor agonists, anti-diabetic agents, anti-hypertensive agents, anti-inflammatory agents, anti-osteoporosis agents, anti-obesity agents, cardiac glycosides, cholesterol lowering agents and thyroid mimetics.

5. The pharmaceutical composition according to claim 3, further comprising at least one nutritional supplement.

* * * * *